United States Patent [19]

Kilkson

[11] Patent Number: 4,588,401

[45] Date of Patent: May 13, 1986

[54] PLATELET STORAGE CONTAINER

[75] Inventor: Henn Kilkson, Wilmington, Del.

[73] Assignee: E. I. Du Pont de Nemours and Company, Wilmington, Del.

[21] Appl. No.: 617,707

[22] Filed: Jun. 6, 1984

Related U.S. Application Data

[63] Continuation of Ser. No. 392,295, Jun. 29, 1982, Pat. No. 4,496,361, which is a continuation-in-part of Ser. No. 290,328, Aug. 5, 1981, abandoned.

[51] Int. Cl.$^4$ .............................................. A61M 5/00
[52] U.S. Cl. .................................................... 604/408
[58] Field of Search ........................ 128/DIG. 24, 1 R; 604/403, 408

[56] References Cited

U.S. PATENT DOCUMENTS

| | | |
|---|---|---|
| 2,702,034 | 2/1955 | Walter . |
| 3,928,294 | 12/1975 | Crawford et al. ......... 128/DIG. 24 |
| 4,140,162 | 2/1979 | Gajewski et al. . |
| 4,191,231 | 3/1980 | Winchell et al. ...................... 150/8 |
| 4,222,379 | 9/1980 | Smith . |
| 4,228,032 | 10/1980 | Talcott ........................... 252/400 R |
| 4,280,497 | 7/1981 | Warner et al. . |

FOREIGN PATENT DOCUMENTS

| | | |
|---|---|---|
| 1862722 | 5/1978 | Belgium . |
| 6076955 | 6/1981 | Japan . |

OTHER PUBLICATIONS

Platelet storage at 22° C., Murphy et al., BLOOD, vol. 46, No. 2, Aug. 1975, pp. 209–218.

*Primary Examiner*—C. Fred Rosenbaum
*Assistant Examiner*—Gene B. Kartchner

[57] ABSTRACT

There is disclosed a platelet storage container made from a copolymeric film material capable of being heat sealed at a low temperature and having specified values for (a) carbon dioxide and oxygen permeabilities, (b) tensile strength, (c) stiffness, (d) seal strength, (e) durability, and (f) thickness.

13 Claims, No Drawings

PLATELET STORAGE CONTAINER

CROSS-REFERENCE TO RELATED APPLICATIONS

This application is a continuation of copending application Ser. No. 392,295, filed on June 29, 1982, now U.S. Pat. No. 4,496,361, which in turn is a continuation-in-part of copending application Ser. No. 290,328, filed on Aug. 5, 1981 now abandoned.

BACKGROUND OF THE INVENTION

Due to the relatively short duration during which platelets can be preserved in a viable state, Federal regulations require that platelets be stored no more than three days at 22° C. before use. It is known that pH commonly falls during storage of blood platelets at 22° C. When the pH reaches 6.0, morphological changes occur in the platelets and viability is lost.

Murphy and Gardner, *Blood*, 46, 209-218 (1975) disclose that when containers constructed of polyvinylchloride are used for storage of platelet concentrations, at 22° C., pH often falls to such low levels (pH <6.0) that viability is lost. They disclose that far lesser degrees of pH fall are observed in bags constructed of polyethylene. From their study of conditions necessary to maintain viability during 3 days storage these authors conclude that (1) pH falls because of the generation of lactic acid by platelet glycolysis and, under some circumstances, the retention of $CO_2$; (2) the rate of pH fall is roughly proportional to the platelet count; (3) polyethylene is more permeable to gases, thereby allowing $CO_2$ escape from and easier $O_2$ entry into the stored platelet concentrates; higher $O_2$ tensions suppress glycolysis by the Pasteur effect; (4) adequate agitation and container size are critical if the beneficial effect of polyethylene is to be obtained; (5) in general, platelets stored in polyethylene containers have excellent viability in vivo although $CO_2$ escape can result in elevations in pH which are deleterious; (6) storage in a 10% $CO_2$ atmosphere prevents these deleterious pH elevations without otherwise impairing platelet viability; and (7) results similar to those achieved with polyethylene can be achieved with polyvinyl chloride if it is made thinner to allow easier penetration of gases.

U.S. Pat. No. 4,140,162, issued to Gajewski et al on Feb. 20, 1979, discloses a clear, autoclavable, blow-moldable plastic formulation for medical and other uses comprising a two, or optionally three, component system including (1) a polyolefin consisting of propylene units as a first component, (2) a block copolymer having thermoplastic rubber characteristics with a central block of ethylenebutylene copolymer and terminal blocks of polystyrene, and (3) an optional third ingredient comprising a softening agent of polyethylene or poly(ethylenevinyl acetate). Blood bags made from the formulation are also disclosed. U.S. Pat. No. 4,222,379 indicates that this formulation exhibits good carbon dioxide transfer characteristics and is suitable for use as transfer bags for storing platelets.

U.S. Pat. No. 4,222,379, issued to Smith on Sept. 16, 1980, discloses a multiple blood bag system which comprises a first bag, a second bag, and conduit means providing sealed flow communication between them. The first bag is made of a plastic material which comprises a different polymer entity from that of the second bag, and the polymer entity of the first bag exhibits the characteristic of suppressing hemolysis of blood cells on long term storage. The patent further discloses that the first (donor) bag may be made of a transparent, flexible, sterilizable material which contains a blood-extractable plasticizer whereas the second (transfer) bag may be made of a translucent, flexible, sterilizable material which is free of blood-extractable plasticizer and may be a material which permits an increased diffusion rate of carbon dioxide during platelet storage so that the pH decrease of the platelets during storage is reduced.

A platelet storage container which permits increased storage time during which viability can be maintained would present definite advantages to the medical profession. Hospitals would be less susceptible to fluctuations in supply versus demand and would suffer less during long weekends when heretofore, because of Federal regulations, the platelet supply quite often had to be nearly depleted before the weekend ended. The provision of such a container from relatively thin material using easy fabrication techniques is a desirable goal offering functional and commercial benefits.

SUMMARY OF THE INVENTION

The present invention provides a platelet storage container made of a copolymeric film material capable of being heat sealed at a low temperature and having an oxygen permeability of at least about $1.8 \times 10^5$ $\mu m^3$ (STP)/($m^2 \cdot sec \cdot Pa$) [100 cc (STP)/(24 hr-atm-100 $in^2$)], a carbon dioxide permeability of from about $4.4 \times 10^5$ to about $8.0 \times 10^5$ $\mu m^3$ (STP)/($m^2 \cdot sec \cdot Pa$) [250 to about 450 cc (STP)/(24 hr-atm-100 $in^2$)], a tensile strength of at least about 8 mPa, a seal strength of at least about 1000 g/cm, a stiffness low enough so that the container can be extended by liquid to a capacity of about 275 ml, a durability sufficient to provide a dart drop value of at least about 100, and a thickness of from about 0.08 mm to about 0.23 mm.

DETAILED DESCRIPTION OF THE INVENTION

In comparison to prior art platelet storage containers, it has been discovered that not only is an increased oxygen permeability desirable and an excessively high $CO_2$ permeability deleterious but that, for maintaining viability for at least 5 days at 22° C. and in many cases 7 days, the oxygen permeability of the material from which the container is constructed must have a certain minimum threshold value and the carbon dioxide permeability must be within a specified range. In addition, the container or its material of construction also has to possess certain other physical properties.

The present invention is an improvement in the platelet storage container used commercially today. Thus, the container of the invention has the same size, shape, and surface area as that presently in commercial use (herein referred to as "standard size, shape and surface area"). It is known that these containers should be extensible so that air does not have to be displaced in order to introduce liquid into the container and air does not have to be introduced in order to remove liquid from the container. In practice, 275 ml of plasma are put into the container which is then centrifuged to separate the plasma and platelets. Thereafter most of the plasma is removed to leave about 2 ml of platelets in about 48 ml of plasma remaining in the container. Hence, the container must be made of a polymeric material having a stiffness low enough that the container can be extended by liquid to a capacity of about 275 ml. In addition to the novel properties set forth herein, the container of the invention also meets this extensibility requirement.

Copolymeric film material which is suitable in constructing a container of the invention has an oxygen permeability of at least about $1.8 \times 10^5$ $\mu m^3$ (STP/(m$^2$·sec·Pa) [100 cc (STP)/(24 hr-atm-100 in$^2$)], preferably at least about $2.7 \times 10^5$ $\mu m^3$ (STP)/(m$^2$·sec·Pa) [150 cc (STP)/(24 hr-atm-100 in$^2$)]. As mentioned previously, platelets are normally stored in units of approximately 50 ml of fluid which is made of about 2 ml of platelets and about 48 ml of plasma. For this 50 ml of fluid, which hereinafter will be called platelet concentrate, the total number of platelets present can vary from about $3 \times 10^{10}$ to greater than $12 \times 10^{10}$. An oxygen permeability of at least about $1.8 \times 10^5$ $\mu m^3$ (STP)/(m$^2$·sec·Pa) [100 cc (STP)/(24 hr-atm-100 in$^2$)] provides sufficient oxygen for about 80% of the total platelet counts encountered during collection and storage of platelets, i.e., sufficient oxygen for total platelet counts as high as $10 \times 10^{10}$. The preferred oxygen permeability value of at least $2.7 \times 10^5$ $\mu m^3$ (STP)/(m$^2$·sec·Pa) [150 cc (STP)/(24 hr-atm-100 in$^2$)] provides sufficient oxygen for about 92% of the total platelet counts encountered during collection and storage, i.e. for total platelet counts as high as $12 \times 10^{10}$.

Copolymeric film materials suitable for constructing the container of the invention should also possess a carbon dioxide permeability of from about $4.4 \times 10^5$ to about $8.0 \times 10^5$ $\mu m^3$ (STP)/(m$^2$·sec·Pa) [250 to about 450 cc (STP)/(24 hr-atm-100 in$^2$], preferably from about $5.3 \times 10^5$ to about $7.3 \times 10^5$ $\mu m^3$ (STP)/(m$^2$·sec·Pa) [300 to about 415 cc (STP)/24 hr-atm-100 in$^2$)]. The $CO_2$ permeability range prescribed above permits escape of sufficient $CO_2$ for 75% of the total platelet counts encountered, i.e., from about $5-10 \times 10^{10}$ platelets, whereas the preferred range provides sufficient $CO^2$ transmission to satisfy 92% of the total platelet counts encountered, i.e., from about $3-12 \times 10^{10}$ platelets. A $CO_2$ permeability below about $4.4 \times 10^5$ $\mu m^3$ (STP)/(m$^2$·sec·Pa) [250 cc (STP)/(24 hr-atm-100 in$^2$)] does not allow sufficient $CO_2$ to escape from the container and thereby results in a buildup of $CO_2$ which causes the pH of the platelet containing fluid to decrease. The prescribed level of $CO_2$ permeability will along with the aforesaid $O_2$ permeability insure that the pH of the platelet concentrate is maintained in the range of about 6.5-7.5 for at least 5 days storage and often up to 7 days when containers having platelets at a total count of about $3-12 \times 10^{10}$ are stored at 22° C. in air. If the $CO_2$ permeability greatly exceeds $8.0 \times 10^5$ $\mu m^3$ (STP)/(m$^2$·sec·Pa) [450 cc (STP)/(24 hr-atm-100 in$^2$)], the pH of the platelet containing fluid may exceed 7.5, thereby resulting in loss of viability. It is to be understood that the permeabilities used herein are those for the copolymeric film material at its selected thickness and are the values obtained by measurement in ambient air.

The copolymeric film material used in constructing the container of the invention has a ratio of carbon dioxide permeability to oxygen permeability of up to about 4.5:1. The preferred range of permeabilities prescribed herein call for rather unusual polymeric films having permeability ratios of 2:1 to 3:1 or less. In contrast thereto, polyvinyl chloride film which is currently used commercially in construction of platelet storage containers has a permeability ratio of about 6.

In addition to the foregoing permeability requirements, the copolymeric film material used in constructing a container of the invention should have a tensile strength of at least about 8 mPa, preferably at least about 9 mPa, and a seal strength of at least about 1000 g/cm. Also, the copolymeric material should be capable of being heat sealed at a low temperature, i.e., from about 125° C. to 140° C., to provide the foregoing seal strength. Fabrication of containers is facilitated by materials which meet this requirement.

The thickness of the copolymeric film material selected for use in constructing the container of the invention will depend on the permeability per mil and the mechanical durability of the polymeric material. For instance, if the material has relatively high oxygen and carbon dioxide permeabilities, then a relatively high thickness can be used. On the other hand, if the oxygen permeability of the material at a particular thickness is marginally low and the carbon dioxide permeability at that thickness falls near the bottom of the prescribed range while the mechanical durability is rather high, then a lower thickness can be employed. In general, the thickness of the material will be from about 0.08 mm to about 0.23 mm. For a copolymer of ethylene and 1-butene or 1-octene having a density of from 0.915 to 0.925 g/cm$^3$, the film material will have a thickness of from about 0.10 mm to about 0.14 mm.

The copolymeric film material should be mechanically durable, i.e., it should be able to withstand vigorous handling at the selected thickness. Generally, suitable materials will have, at the selected thickness, a dart drop value of at least about 100 as measured by the procedure of ASTM 1709.

The material of construction must also be compatible with plasma protein. By "compatible" it is meant that the material does not interact with the plasma or leach into the plasma materials which are deleterious to the plasma, platelets or recipient. The polymeric material should have a water vapor transmission of less than about 25 g/24 hr/m$^2$ at 48° C. (100° F.) and 90% relative humidity as measured by ASTM-E96 test.

As used herein, the expression "copolymeric film material" means a film material in which each layer is made from a single copolymer or homopolymer and at least one layer is made from a single copolymer. Polymeric materials suitable for use in constructing a container of the invention are at least translucent and include the following:

copolymers of ethylene and an α-olefin of 4–10 carbon atoms having a density of from 0.915–0.925 g/cm$^3$ (a so-called linear low density polyethylene), typical α-olefins include 1-butene, hexene, 1-octene and 1-decene;

ionomers, such as sodium or zinc neutralized copolymers of ethylene and acrylic or methacrylic acid or derivatives thereof; and laminates or coextrudates of ionomers/polyester elastomers and linear low density polyethylene elastomers.

Preferably, the material of construction is a copolymer of ethylene and an α-olefin of 4–10 carbon atoms having a density of from 0.915–0.925 g/cm$^3$. These copolymers of ethylene and the 4–10 carbon atoms α-olefin have about 3-5 mole percent of the latter component. Preferably, the α-olefin is 1-butene or 1-octene with 1-octene being more preferred. These preferred materials give the container an improved clarity. These materials display a haze of 12 to 15%.

When storing platelet concentrate in the container of the invention adequate agitation is provided as is customary in the art. Agitation can be effected by methods well known in the art such as by use of a to-and-fro flat bed agitator operated at about 70 cpm or a "ferris-wheel" agitator operated at about 5 rpm.

Platelet storage containers presently used commercially in the trade have a surface area of about 277 cm$^2$ (43 in$^2$). The container normally bears a label having an area of about 77 cm$^2$ (12 in$^2$) and which covers about 28% of the container's surface area. This label reduces the permeability of the container in this area. The permeability requirements set forth herein are for the container without a label. Although presently for commercial use the label is adhered completely to the surface of the container, the label could also be attached at only one of its ends, to a flap specially made on the container, or in a manner so as not to mask any of the useful surface area of the container. If the label is to be adhered completely to the surface of the container, the permeability of the polymeric material used in constructing the container must be such as to compensate for the diminution in permeability caused by the label.

Although the present invention is not limited by theory, it is believed that the foregoing permeability requirements are sufficient to assure the platelet storage container adequate, effective permeability, $\bar{P}_{eff}$, during use to provide ingress of enough oxygen and egress of enough carbon dioxide to maintain platelet viability of at least five days and in many cases up to seven days. The effective permeability is given by inverse addition:

$$\frac{1}{\bar{P}_{eff}} = \frac{1}{\bar{P}_{film}} + \frac{1}{\bar{P}_{l.r.}} + \frac{1}{\bar{P}_{label}}$$

where $\bar{P}_{label}$ acts only in the area of the label and $\bar{P}_{l.r.}$ is the liquid resistance permeability. In the present invention $\bar{P}_{eff}$ for oxygen, $\bar{P}_{eff}$, O$_2$, should be at least about $1.2 \times 10^5$ μm$^3$ (STP)/(m$^2$·sec·Pa) [66 cc/(24 hr-atm-100 in$^2$)] and preferably is at least about $1.3 \times 10^5$ (74). The O$_2$ permeability of $1.8 \times 10^5$ μm$^3$ (STP)/(m$^2$·sec·Pa) [100 cc/(24 hr-atm-100 in$^2$)] set forth earlier herein guarantees a $\bar{P}_{eff}$, O$_2$ of at least about $1.2 \times 10^5$ μm$^3$ (STP)/(m$^2$·sec·Pa) [66 cc/(24 hr-atm-100 in$^2$)].

Since blood banks often do not know beforehand what platelet count to expect, the container of the invention provides assurance that for about 75-80% of the total platelet counts encountered, platelet viability will be maintained for at least five days and in many cases up to seven days when storage is effected at 22° C. Moreover, the preferred permeabilities set forth herein provide such viability for about 92% of the total platelet counts encountered.

The platelet storage container of the invention will normally have the shape of a bag. When a multiple bag system is desired, the platelet storage container of the invention can be sterilely connected to other bags by using the sterile docking system described and claimed in commonly assigned copending U.S. patent application Ser. No. 267,291, filed on June 4, 1981. Since the platelet storage container of the invention is made from a copolymeric film rather than a polymeric blend, the film is homogeneous and provides relatively consistent permeabilities. Moreover, the fabrication of the container from a film rather than by use of blow-molding techniques provides more uniform wall thickness and, hence, less variation in permeabilities at different positions on the container.

Test Methods

The properties prescribed herein for the container of the invention are measured as set forth below.
1. Permeability—ASTM D-1434
2. Tensile strength—ASTM D-882
3. Seal Strength—

Film samples are heat sealed by conventional means to give welded seals with minimal flow out of the seal area. Two sheets of the same material are first heat sealed with a hot bar along a line to form a sealed pair. A sample 2.54 cm wide is cut from near the center portion of the sealed pair so that the seal line is near one end of the sample. The resulting free distal ends of the sample are attached to the grips of a peel tester which gives substantially an impact test on the seal and measures the strength of the seal in grams per width of the seal.

4. Viability—

As used herein "viability" means the capacity of platelets to circulate in vivo. An in vivo determination of viability can be made by $^{51}$Cr labelling of platelets and reinfusing them into the original normal volunteer. As used herein viability is determined by measurement of shape change, morphology score, dispersion of platelet size distribution, and percent aggregation. Shape change measures the deviation from discoid shape which is the normal shape of platelets and is determined by light transmission analysis using a technique similar to that described by Holme and Murphy, *Journal of Laboratory and Clinical Medicine*, 92, pp. 53–64 (1978). Dispersion tests measure the degree of fragmentation of platelets and is determined with a Coulter Counter using a method similar to that described by Holme et al, *Blood*, 52, 425–435 (1978). Morphology score, which gives the percentage of discoid shape, is determined by phase-contrast microscopy. Percent aggregation indicates the ability of platelets to perform hemostatic function and is also determined by light transmission. Test methods used for morphology score and aggregation were similar to those set forth in the aforesaid Holme et al article.

Murphy, AABB Meeting in Montreal, Nov. 9-12, 1980, has shown that shape change and dispersion correlate quantitatively with in vivo survival measured by reinfusion of $^{51}$Cr labeled platelets into the original normal volunteer (% $^{51}$Cr recovery in vivo). The shape change was used as an in vitro measure of projected recovery. Murphy reported that morphology score is conceded to be similarly a good measure of platelet survival. There have been few instances where morphology score was good but platelets failed to circulate and no known instances where morphological measurements either in the form of shape change or visual counting were poor whereas in vivo results were good. According to Murphy's findings, a shape change of 1.07 corresponds to ~30% in vivo recovery; shape change is linearly related to in vivo recovery; and a shape change of 1.21 corresponds to a 65% recovery.

A morphology score of 300 on a scale of 1 to 800 is considered the minimum acceptable value and corresponds to 25-30% recovery. The morphology score immediately after platelets are harvested ranges from about 650–700 and the corresponding recovery ($^{51}$Cr) is 65–75%. Thus, one can surmise that in the range 300–700 the % in vivo recovery is estimated by morphology score/10.

The invention is further illustrated by the following examples in which all temperatures are in degrees Celsius and all percentages, except % in vivo recovery, are by weight unless otherwise stated. The percentage of in vivo recovery is by number. Platelet count values and permeability measurements each have a precision of about ±20%. Values for pH given in the examples are as measured at 22° C.

EXAMPLES 1-5

Platelet storage bags of standard size, shape and surface area are made from films of the following copolymeric film materials:

(a) a copolymer of ethylene (about 97 mole %) and 1-butene (LLDPE) having a density of 0.919 g/cm$^3$, (b) coextrudate of 20% polybutylene (polytetramethylene glycol) terephthalate (10–30% polyether) and 80% LLDPE, and (c) a copolymer of ethylene and 1-octene (LLDPE) having a density of 0.918 g/cm$^3$.

The properties of the resulting platelet storage bags are given in the Table. Each bag has a stiffness low enough so that it could be extended by liquid to a capacity of about 275 ml.

TABLE

PLATELET STORAGE BAG PROPERTIES

| Example | Composition | Thickness, mm (mil) | $\bar{P}_{O_2}$ ($\times 10^{-5}$) | $\bar{P}_{CO_2}$ ($\times 10^{-5}$) | $\bar{P}_{CO_2}/\bar{P}_{O_2}$ | Seal Strength, (g/cm) | Tensile Strength, mPa |
|---|---|---|---|---|---|---|---|
| 1 | a | 0.1 (3.9) | 2.5 | 7.3 | 2.9 | — | 12.2 |
| 2 | a | 0.12 (4.9) | 1.8 | 5.3 | 3.0 | >1180 | 12.2 |
| 3 | a | 0.14 (5.7) | 2.0 | 5.7 | 2.8 | >1180 | 12.3 |
| 4 | b | 0.13 (5) | 2.0 | 6.4 | 3.2 | >1180 | 11.6 |
| 5 | c | 0.12 (4.9) | 2.6 | 7.9 | 3.0 | >1180 | 11.7 |

Permeability units are $\mu m^3$ gas (STP)/(m$^2$ · sec · Pa).
For seal strength a value >1180 g means sample did not fail at the limit of the tester.

EXAMPLE 6

Using 4 bags similar to that described in Example 3 about 50 ml of platelet concentrate are stored in each for 7 days at 22° with flat bed agitation. The platelet concentration in the bags ranged from about 1.2–1.7×10$^9$/cc. The shape change is measured at 1, 3 and 7 days by taking a 1–4 ml sample from each bag at each of these time periods. The maximum pH on the first day is 7.36 and the minimum pH on the seventh day is 7.12. The 7-day mean shape change is 1.16 which corresponds to a projected in vivo platelet recovery of 55%.

EXAMPLE 7

Using 10 bags similar to that described in Example 3 about 50 ml of platelet concentrate are stored in each for 7 days at 22° with ferris-wheel agitation. The platelet concentration in the bags ranges from 0.96–2.77×10$^9$/cc and the range of total platelet count is from 5.7–13×10$^{10}$. The morphology score is measured at 3 and 7 days by taking a 1–4 ml sample from each bag at each of these time periods. The 10-bag average morphology score on day 7 is about 490 which corresponds to a projected in vivo platelet recovery of 49%. The platelet concentrate has an average pH of 7.2 at 3 days and 7.07 at 7 days.

CONTROL

About 50 ml of platelet concentrate are stored at 22° for 7 days in each of ten prior art platelet storage bags of standard size, shape and surface area. The bags are constructed from polyvinyl chloride film having a thickness of 0.38 mm (15 mil). The oxygen and carbon dioxide permeabilities of the film are 7.1×10$^4$ and 4.2×10$^5$ $\mu m^3$ (STP)/(m$^2$·sec·Pa) (40 and 240 cc (STP)/(24 hr-atm-100 in$^2$)], respectively. The film has a tensile strength of about 20 mPa and a seal strength of about 1200 g/cm. Each bag had a stiffness low enough so that it could be extended by liquid to a capacity of about 275 ml. The platelet concentration in the bags ranges from 0.86–2.50×10$^9$/cc and the range of total platelet count is 4.64–11.5×10$^{10}$. The 10-bag average, 7-day morphology score is 249 corresponding to a projected in vivo platelet recovery of 25%. The platelet concentrate has an average pH of 6.6 at 3 days and 6.1 at 7 days.

EXAMPLE 8

Using 9 bags similar to that described in Example 5 about 50 ml of platelet concentrate are stored in each for 7 days at 22° with flat-bed agitation. The platelet concentration in the bags ranges from 1.22–2.49×10$^9$/cc and the range of total platelet count is from 5.9–12.6×10$^{10}$. The morphology score is measured at 0, 3, 5 and 7 days by taking a 1–3 ml sample from each bag at each of these time periods. The 9-bag average morphology score on day 7 is 517 which corresponds to a projected in vivo platelet recovery of 52%. The platelet concentrate has an average pH of 7.18, 7.27, 7.18 and 6.97 at 0, 3, 5 and 7 days, respectively.

EXAMPLE 9

Using 7 bags similar to that described in Example 5 about 50 ml of platelet concentrate are stored in each bag for 7 days at 22°, with elliptical agitation. The platelet concentration in the bags ranges from 1.10–2.55×10$^9$ and the range of total platelet count is from 5.3–12.9×10$^{10}$. The morphology score is measured at 0, 3, 5 and 7 days by taking a 1–3 ml sample from each bag at each of these time periods. The 7-bag average morphology score on day 7 is 515 which corresponds to a projected in vivo platelet recovery of 52%. The platelet concentrate has an average pH of 7.18, 7.30, 7.12 and 7.02 at 0, 3, 5 and 7 days, respectively.

I claim:

1. A platelet storage container made from a copolymeric film material capable of being heat sealed at a low temperature and having an oxygen permeability of at least about 1.8×10$^5$ $\mu m^3$ (STP)/(m$^2$·sec·Pa), a carbon dioxide permeability of from about $4.4 \times 10^5$ to about $8.0 \times 10^5$ $\mu m^3$ (STP)/($m^2 \cdot sec \cdot Pa$), a tensile strength of at least about 8 mPa, a seal strength of at least about 1000 g/cm, a stiffness low enough that the container can be extended by liquid to a capacity of about 275 ml, a durability sufficient to provide a dart drop value of at least about 100, and a thickness of from about 0.08 to about 0.23 mm.

2. A container according to claim 1 wherein the copolymeric film material has an oxygen permeability of at least $2.7 \times 10^5$ $\mu m^3$ (STP)/($m^2 \cdot sec \cdot Pa$).

3. A container according to claim 2 wherein the copolymeric film material has a carbon dioxide permeability of from about $5.3 \times 10^5$ to about $7.3 \times 10^5$ $\mu m^3$ (STP)/($m^2 \cdot sec \cdot Pa$).

4. A container according to claim 3 wherein the copolymeric film material has a tensile strength of at least about 9 mPa.

5. A platelet storage container made from a copolymeric film material selected from the group consisting of:

(a) copolymers of ethylene and an α-olefin of 4–10 carbon atoms having a density of from 0.915–0.925 g/cm$^3$;

(b) ionomers; and (c) laminates or coextrudates of an ionomer/polyester elastomer and a linear low density polyethylene elastomer, said copolymeric film material being capable of being heat-sealed at a low temperature and having an oxygen permeability of at least about $1.8 \times 10^5$ $\mu m^3$ (STP)/($m^2 \cdot sec \cdot Pa$), a carbon dioxide permeability of from about $4.4 \times 10^5$ to about $8.0 \times 10^5$ $\mu m^3$ (STP)/($m^2 \cdot sec \cdot Pa$), a tensile strength of at least about 8 mPa, a seal strength of at least about 1000 g/cm, a stiffness low enough that the container can be extended by liquid to a capacity of about 275 ml, a durability sufficient to provide a dart drop value of at least about 100, and a thickness of from about 0.08 to about 0.23 mm.

6. A container according to claim 5 wherein the copolymeric film material is a copolymer of ethylene and an α-olefin of 4–10 carbon atoms having a density of from 0.915–0.925 g/cm$^3$.

7. A container according to claim 6 wherein the α-olefin of 4–10 carbon atoms is 1-butene or 1-octene and said copolymeric film material has a thickness of from about 0.10 mm to about 0.14 mm.

8. A container according to claim 7 wherein the α-olefin is 1-octene.

9. A platelet storage container made from a copolymeric film material capable of being heat-sealed at a low temperature and having an oxygen permeability of at least about $1.8 \times 10^5$ $\mu m^3$ (STP)/($m^2 \cdot sec \cdot Pa$), a carbon dioxide permeability of from about $4.4 \times 10^5$ to about $8.0 \times 10^5$ $\mu m^3$ (STP)/($m^2 \cdot sec \cdot Pa$), a tensile strength of at least about 8 mPa, a seal strength of at least about 1000 g/cm, a stiffness low enough that the container can be extended by liquid to a capacity of about 275 ml, a durability sufficient to provide a dart drop value of at least about 100, and a thickness of from about 0.08 to about 0.23 mm; and said container being capable of maintaining platelet viability from 5–7 days at 22° C.

10. A container according to claim 5 wherein the copolymeric film material has a tensile strength of at least about 9 mPa.

11. A container according to claim 10 wherein the copolymeric film material is a copolymer of ethylene and an α-olefin of 4–10 carbon atoms having a density of from 0.915–0.925 g/cm$^3$.

12. A container according to claim 11 wherein the α-olefin of 4–10 carbons is 1-butene or 1-octene and said polymeric film material has a thickness of from about 0.10 mm to about 0.14 mm.

13. A container according to claim 12 wherein the α-olefin is 1-octene.

* * * * *